US00PP35933P2

(12) United States Plant Patent
Smit

(10) Patent No.: US PP35,933 P2
(45) Date of Patent: Jul. 2, 2024

(54) ***TRADESCANTIA* PLANT NAMED 'EC-TRAD-2303'**

(50) Latin Name: *Tradescantia cerinthoides*
Varietal Denomination: EC-TRAD-2303

(71) Applicant: Eden Collection, BV, Sappemeer (NL)

(72) Inventor: Obed Jacob Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 18/387,392

(22) Filed: Nov. 6, 2023

(51) Int. Cl.
*A01H 5/12* (2018.01)
*A01H 6/00* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Cassandra Bright

(57) ABSTRACT

A new and distinct cultivar of *Tradescantia* plant named 'EC-TRAD-2303' is disclosed, characterized by bright white and green variegated foliage, with large, pointed, elongated leaves. White flowers bloom continuously when grown indoors. The new variety is a *Tradescantia*, typically used as an ornamental plant.

3 Drawing Sheets

Latin name of the genus and species: *Tradescantia cerinthoides.*

Variety denomination: 'EC-TRAD-2303'.

BACKGROUND OF THE INVENTION

The new cultivar is a product of a naturally-occurring branch mutation of *Tradescantia cerinthoides* '200409', unpatented. The new variety was discovered by the inventor in March of 2021, at a nursery in Sappemeer, the Netherlands.

Asexual reproduction of the new cultivar 'EC-TRAD-2303' by stem-top cuttings was first performed at the same nursery in Sappemeer, the Netherlands in April 2021, and has shown that the unique features of this cultivar are stable and reproduced true to type through successive generations.

SUMMARY OF THE INVENTION

The cultivar 'EC-TRAD-2303' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-TRAD-2303'. These characteristics in combination distinguish 'EC-TRAD-2303' as a new and distinct *Tradescantia* cultivar:

1. Bright white and fresh green variegated leaf-color.
2. Large, elongated leaves, pointed to the end.
3. Strong and thick stems.

PARENT COMPARISON

Plants of the new cultivar 'EC-TRAD-2303' are similar to plants of the parent variety in most horticultural characteristics, however, plants of the new cultivar 'EC-TRAD-2303' differ from in the following characteristics:

1. Leaf color of the new variety is white and green, while the leaf color of the parent variety is white and darker green.
2. Leaves of the new variety are larger and more elongated than leaves of the parent variety.
3. Stems of the new variety are stronger and thicker than stems of the parent variety.

COMMERCIAL COMPARISON

Plants of the new cultivar 'EC-TRAD-2303' are similar to plants of the commercial variety *Tradescantia albiflora* 'Nanouk', U.S. Plant Pat. No. 29,711. However, plants of the new cultivar differ in the following characteristics:

1. Leaf color of the new variety is white and green, while the leaf color of this comparator is purple, green and greyed-green.
2. Leaves of the new variety are larger than leaves of this comparator.

Plants of the new cultivar 'EC-TRAD-2303' are similar to plants of the unpatented *Tradescantia cerinthoides* 'EC-TRADE-2011' U.S. Plant Pat. No. 33,788. However, plants of the new cultivar differ in the following characteristics:

1. Leaf color of the new variety is white and green, while the leaf color of this comparator is green with pink stripes.
4. Leaves of the new variety are larger than leaves of this comparator.
5. Plants of the new variety are less compact than plants of this comparator.

BRIEF DESCRIPTION OF THE PHOTOGRAPHS

The accompanying photograph in FIG. 1 illustrates in full color a typical plant of 'EC-TRAD-2303' grown in a glass greenhouse in Sappemeer, the Netherlands. The plant is approximately 8 weeks of age.

Figure 1:
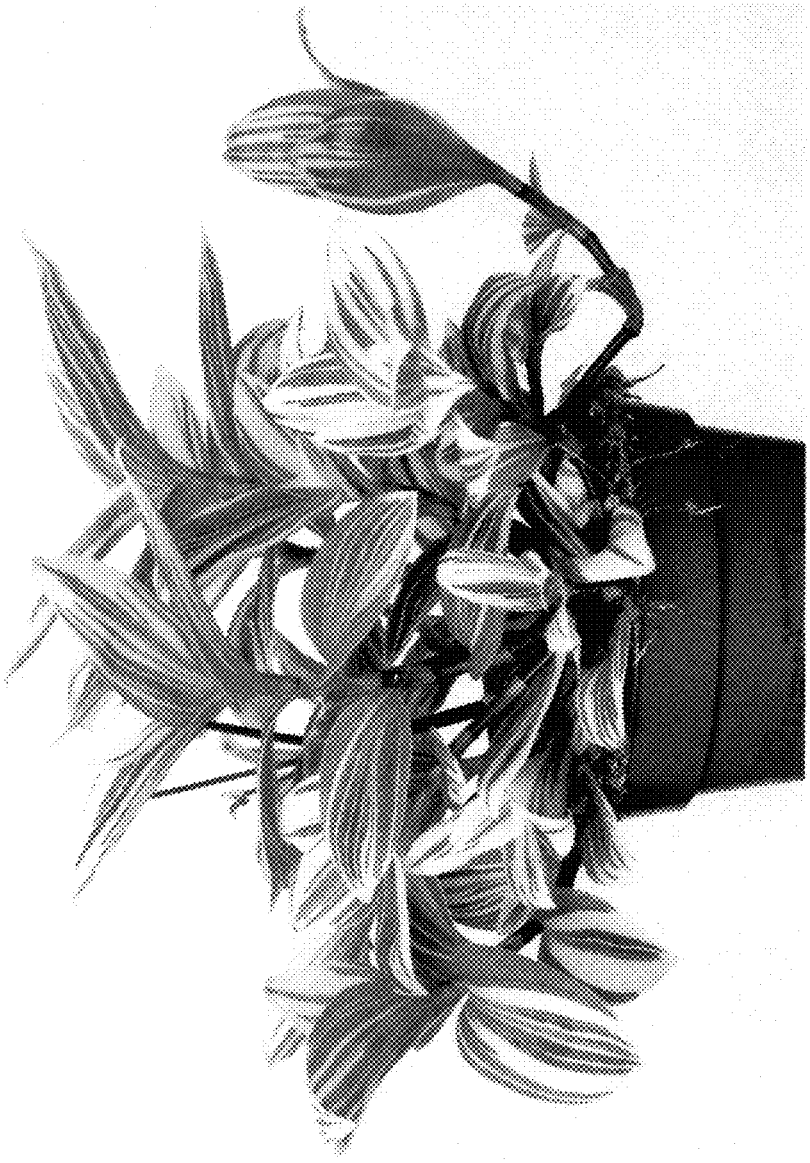
Figure 2:
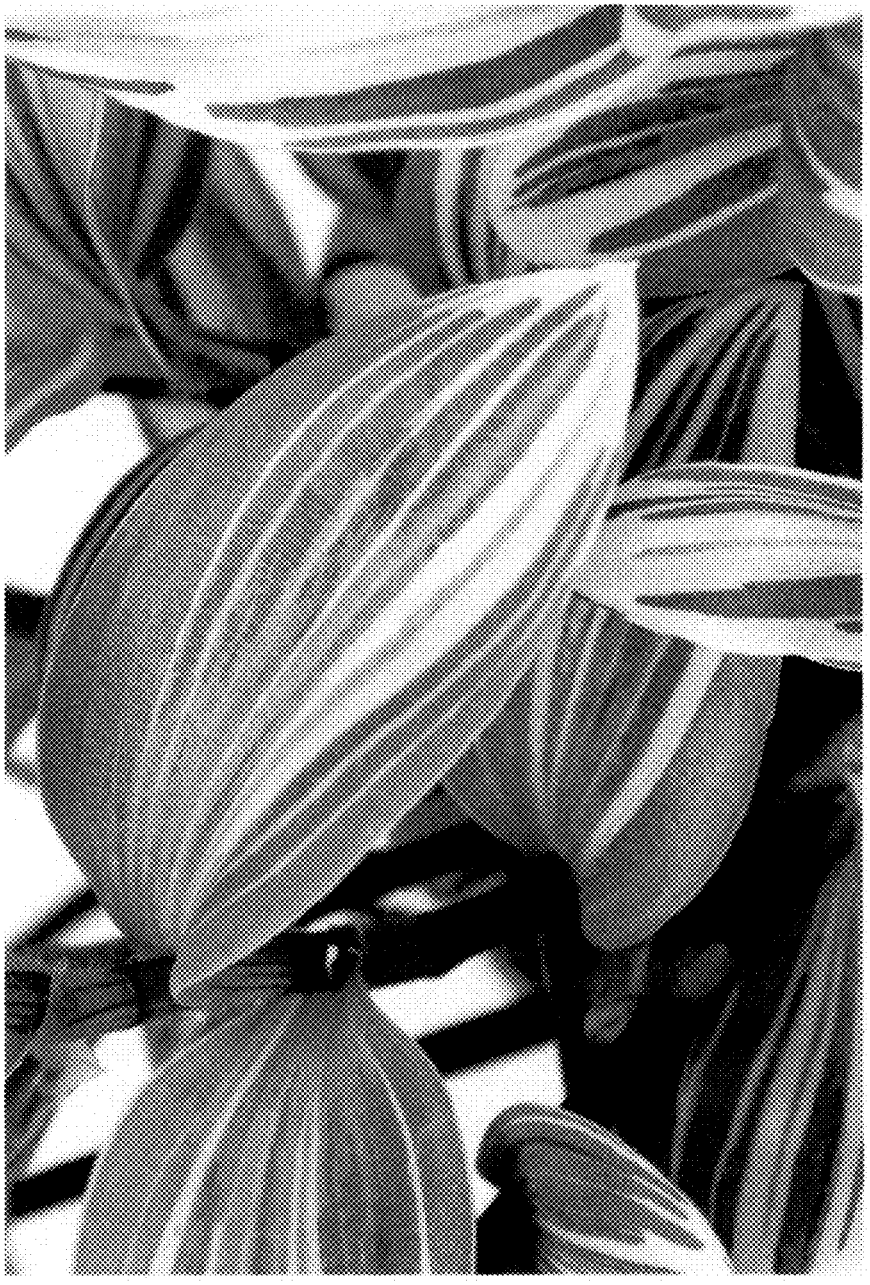
FIG. 2 illustrates a close up of the foliage.
Figure 3:
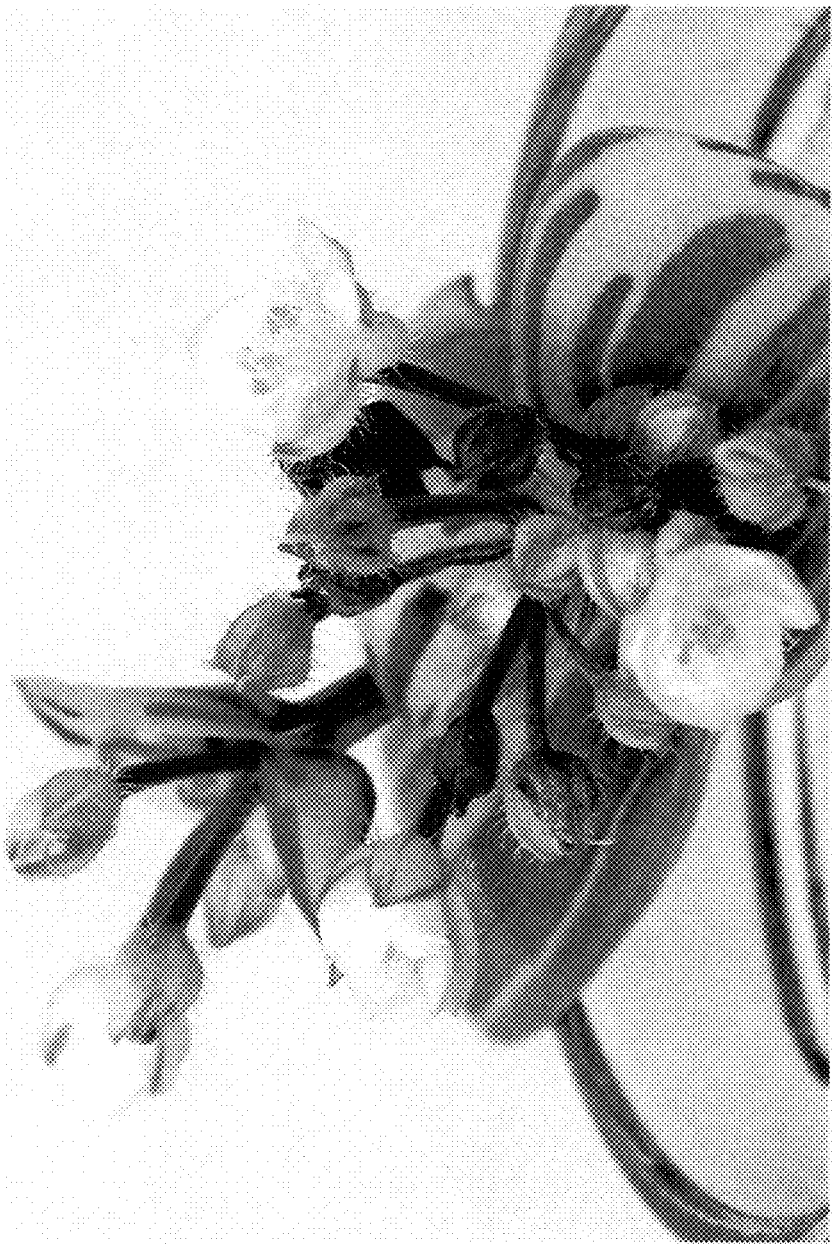
FIG. 3 illustrates flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-TRAD-2303' plants at 8 weeks of age, grown in a glass greenhouse in Sappemeer, the Netherlands. Measurements and numerical values represent averages of typical types.

Botanical classification: *Tradescantia cerinthoides* 'EC-TRAD-2303'.

PROPAGATION

Time to initiate roots: 10 days at 18° C. in summer, 14 days at 18° C. in winter.

Description of roots: Fine, herbaceous, moderately dense, freely branching. White in color, not accurately measured with R.H.S. chart.

PLANT

Plant type: Perennial potted plant.
Container size: 7 cm.
Growth habit: Broad spreading, upright.
Height: Average 16.8 cm to top of foliar plane; 13.8 cm to top of floral plane.
Plant spread: Average 29.3 cm.
Growth rate: Moderate.
Vigor: Moderately high.
Quantity of main branches: Average 10.
Quantity of lateral branches: Average 7.
Branching habit: Basal branching; main branches grow from the base, with lateral branches. Pinching not required but will improve branching when performed.
Internode length: Average 2.8 cm.
Main branches:
- *Length*.—Average 11.1 cm.
- *Diameter*.—Average 0.4 cm.

Stem:
- *Appearance and shape*.—Rounded, glabrous.
- *Length*.—Average 2.8 cm.
- *Diameter*.—Up to 9 mm.
- *Aspect*.—Average 45° from vertical.
- *Color*.—RHS Green 137C.
- *Strength*.—Moderately weak.
- *Texture*.—Glabrous.
- *Pubescence*.—None.
- *Color, developing*.—RHS Yellow-Green 148B to 148C, axially striped Purple N77C.
- *Color, mature*.—RHS Yellow-Green 146A to 146B, axially striped Purple N77B.
- *Color at internodes*.—RHS Purple N77B and N79B.

FOLIAGE

Leaf:
- *Arrangement*.—Distichous, single.
- *Quantity*.—Average 6 per lateral branch.
- *Length*.—Average 7.9 cm, excluding sheath.
- *Width*.—Average 3.6 cm.
- *Sheath length*.—Average 0.7 cm.
- *Sheath width*.—Average 0.5 cm.
- *Sheath color*.—Transparent RHS Greyed-White 156B and 156C, veined Purple N77B.
- *Shape*.—Ovate to elliptic.
- *Aspect*.—Slightly concave.
- *Apex*.—Acute.
- *Base*.—Cuneate, sheathing.
- *Margin*.—Entire.
- *Texture*.—Upper Side: Glabrous, smooth, slightly velvety. Under Side: Glabrous, smooth, moderately velvety.
- *Pubescence*.—Sheath densely covered with soft, thin hairs, average length 0.2 cm, colored transparent RHS Greyed-White 156A.
- *Rugosity*.—Both sides non-rugose.
- *Luster*.—Upper Side: Very slightly glossy, slightly velvety. Under Side: Slightly to moderately glossy, moderately velvety.
- *Color*.—Young Foliage Upper Side: RHS White NN155B, irregularly axially striped Yellow-Green 144A. Young Foliage Under Side: RHS White NN155B, irregularly axially striped Green 138A. Mature Foliage Upper Side: RHS Green 137B and 138A, irregularly axially striped White NN155C. Mature Foliage Under Side: RHS Green 138B to Greyed-Green 191A, irregularly axially striped White NN155D.

Venation:
- *Type*.—Parallel.
- *Color*.—Upper Side: Colored as leaf blade. Under Side: Colored as leaf blade, main vein RHS Yellow-Green 143B.

FLOWER

Natural flowering season: Flowers continuously indoors.
Inflorescence type: Terminal cluster.
Quantity of flowers per inflorescence: Average 10.
Quantity of flowers per plant: Average 30.
Quantity of buds per plant: Average 20.
Quantity of flowers and buds per plant: Average 50.
Inflorescence size:
- *Height*.—Average 5 cm.
- *Diameter*.—Average 2.6 cm.

Flower:
- *Type and form*.—Single, rotate.
- *Habit*.—Low to moderate.
- *Length*.—Average 0.6 cm.
- *Height*.—Average 1.2 cm.
- *Diameter*.—Average 1.2 cm.
- *Shape*.—Rotate.
- *Aspect*.—Upright to outward.
- *Fragrance*.—None.
- *Persistence*.—Self-cleaning.
- *Longevity*.—Average 5 days on plant.

Petals:
- *Quantity*.—Average 3.
- *Whorls*.—Average 1.
- *Length*.—Average 0.6 cm.
- *Width*.—Average 0.6 cm.
- *Shape*.—Broad ovate.
- *Margin*.—Entire.
- *Apex*.—Acute.

*Base*.—Cuneate.
*Texture*.—Upper Surface: Smooth, glabrous, moderately velvety. Lower Surface: Smooth, glabrous, slightly velvety.
*Rugosity*.—Both sides non-rugose.
*Luster*.—Upper Surface: Matte. Lower Surface: Very slightly glossy.
*Color*.—When Opening: Upper Surface: RHS White NN155D. Lower Surface: RHS White NN155D. Fully Opened: Upper Surface: RHS White NN155D. Lower Surface: RHS White NN155D.

Bud:
*Shape*.—Broad ovate, 3-sided.
*Length*.—Average 0.4 cm.
*Diameter*.—Average 0.3 cm.
*Texture*.—Smooth, moderately covered with soft, thin hairs, average length 0.1 cm, colored transparent RHS White N155A.
*Luster*.—Matte, slightly velvety.
*Color*.—RHS White NN155B, axially striped and tipped Yellow-Green 144A.
*Surface*.—Pubescent.

Calyx:
*Shape*.—Rotate.
*Length*.—Average 0.2 cm.
*Diameter*.—Average 0.8 cm.

Sepals:
*Arrangement*.—Rotate.
*Quantity*.—Average 3.
*Whorls*.—Average 1.
*Length*.—Average 0.4 cm.
*Width*.—Average 0.25 cm.
*Shape*.—Narrow ovate, strongly concave.
*Tip*.—Acute.
*Base*.—Cuneate.
*Margin*.—Entire.
*Color*.—When Opening: Upper Surface: RHS White NN155B, tipped Yellow-Green 144A. Lower Surface: RHS White NN155D, tipped Yellow-Green 144A. Fully Opened: Upper Surface: RHS White NN155D, tipped Yellow-Green 144A. Lower Surface: RHS White NN155D, tipped Yellow-Green 144A.
*Texture*.—Upper Surface: Smooth, glabrous. Under Surface: Smooth, sparsely covered with soft, thin hairs, average length 0.1 cm, colored transparent RHS White NN155D.
*Luster*.—Upper Surface: Matte. Under Surface: Slightly glossy.

Pedicel:
*Length*.—Average 0.9 cm.
*Diameter*.—Average 0.75 mm.
*Angle*.—Average 30°.
*Color*.—RHS Purple N79B.
*Texture*.—Smooth, glabrous.
*Luster*.—Slightly glossy.
*Strength*.—Moderately weak.

REPRODUCTIVE ORGANS

Gynoecium:
*Pistil number*.—Average 1.
*Pistil length*.—Average 0.5 cm.
*Stigma shape*.—Pointed.
*Stigma length*.—Average 0.02 cm.
*Stigma diameter*.—Average 0.02 cm.
*Stigma color*.—RHS White NN155D.
*Style length*.—Average 0.48 cm.
*Style color*.—RHS White NN155D.
*Ovary color*.—RHS White N155A.

Androecium:
*Stamen number*.—Average 6.
*Filament length*.—Average 0.3 cm.
*Filament color*.—RHS White NN155D.
*Anther shape*.—Dorsifixed, flattened kidney shape.
*Anther length*.—Average 0.8 mm.
*Anther width*.—Average 0.5 mm.
*Anther color*.—RHS Yellow 12A.
*Pollen quantity*.—Low.
*Pollen color*.—RHS Yellow 13B.

OTHER CHARACTERISTICS

Flower: At the base of the filaments soft, thin hairs are present (typical for *Tradescantia*), average length: 0.45 cm, colored RHS White NN155D.
Seeds and fruits: None observed to date.
Disease/pest resistance: No increased nor decreased resistance nor susceptibility to normal diseases and pests of *Tradescantia* has been observed.
Temperature tolerance: Tolerant to 40° C.; hardy to USDA zones 10 to 12. Moderate tolerance to rain and wind.

What is claimed is:

1. A new and distinct cultivar of *Tradescantia* plant named 'EC-TRAD-2303' as herein illustrated and described.

* * * * *